(12) United States Patent
Ritscher et al.

(10) Patent No.: US 7,536,224 B2
(45) Date of Patent: May 19, 2009

(54) METHOD FOR ELIMINATION OF VENTRICULAR PRO-ARRHYTHMIC EFFECT CAUSED BY ATRIAL THERAPY

(75) Inventors: David E. Ritscher, Minneapolis, MN (US); Jeffrey M. Gillberg, Coon Rapids, MN (US); Mark L. Brown, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 846 days.

(21) Appl. No.: 10/426,765

(22) Filed: Apr. 30, 2003

(65) Prior Publication Data
US 2004/0220624 A1 Nov. 4, 2004

(51) Int. Cl.
*A61N 1/362* (2006.01)

(52) U.S. Cl. .................................................. 607/14

(58) Field of Classification Search ............... 607/5–14, 607/119, 4
See application file for complete search history.

(56) References Cited

U.S. PATENT DOCUMENTS

| | | | |
|---|---|---|---|
| 4,170,999 A | 10/1979 | Allen et al. ............ 128/419 PG |
| 4,375,817 A | 3/1983 | Engle et al. | |
| 4,384,505 A | 5/1983 | Cotton, Jr. et al. | |
| 4,387,717 A | 6/1983 | Brownlee et al. ...... 128/419 PG |
| 4,511,633 A | 4/1985 | Bruno et al. | |
| 4,577,633 A | 3/1986 | Berkovits et al. | |
| 4,587,970 A | 5/1986 | Holley et al. | |
| 4,726,380 A | 2/1988 | Vollmann et al. | |
| 4,830,006 A | 5/1989 | Haluska et al. | |
| 4,880,005 A | 11/1989 | Pless et al. | |
| 4,949,719 A | 8/1990 | Pless et al. | |
| 5,107,850 A | 4/1992 | Olive | |
| 5,117,824 A | 6/1992 | Keimel et al. | |
| 5,161,527 A | 11/1992 | Nappholz et al. | |
| 5,188,105 A | 2/1993 | Keimel | |
| 5,228,437 A | 7/1993 | Schroeppel ........... 128/419 PG |
| 5,265,601 A | 11/1993 | Mehra ............................ 607/9 |
| 5,312,441 A | 5/1994 | Mader et al. | |
| 5,313,953 A | 5/1994 | Yomtov et al. | |
| 5,480,413 A * | 1/1996 | Greenhut et al. .............. 607/14 |
| 5,545,186 A | 8/1996 | Olson et al. | |

(Continued)

FOREIGN PATENT DOCUMENTS

WO WO 95/28987 A1 11/1995

(Continued)

OTHER PUBLICATIONS

Koyrakh L., et al. "Wavelet transform based algorithms for EGM morphology discrimination of implantable ICDs". *Computers in Cardiology*. 2000;26:343-346.

*Primary Examiner*—George R Evanisko
(74) *Attorney, Agent, or Firm*—Stephen W. Bauer; Michael C. Soldner

(57) ABSTRACT

A system and method are provided for controlling atrial antitachycardia pacing (ATP) delivery based on detection of ventricular pro-arrhythmia during or immediately after atrial ATP. Ventricular pro-arrhythmia is detected based on one or more criteria relating to pro-arrhythmic changes including, but not limited to, ventricular rate changes, R-wave morphology changes, and/or 1:1 or nearly 1:1 atrial-ventricular conduction patterns persisting at high ventricular rates. Upon detecting ventricular pro-arrhythmia, a current atrial ATP sequence is aborted. Atrial ATP therapies may subsequently be temporarily or permanently disabled.

9 Claims, 10 Drawing Sheets

U.S. PATENT DOCUMENTS

| | | | |
|---|---|---|---|
| 5,560,369 A | 10/1996 | McClure et al. | |
| 5,620,471 A * | 4/1997 | Duncan | 607/14 |
| 5,720,295 A | 2/1998 | Greenhut et al. | |
| 5,755,736 A | 5/1998 | Gillberg et al. | |
| 5,755,737 A | 5/1998 | Prieve et al. | |
| 5,893,882 A * | 4/1999 | Peterson et al. | 607/14 |
| 5,931,857 A * | 8/1999 | Prieve et al. | 607/14 |
| 5,987,352 A | 11/1999 | Klein et al. | |
| 5,987,356 A * | 11/1999 | DeGroot | 607/5 |
| 6,091,991 A * | 7/2000 | Warren | 607/14 |
| 6,330,477 B1 * | 12/2001 | Casavant | 607/14 |
| 6,393,316 B1 | 5/2002 | Gillberg et al. | |
| 6,400,986 B1 | 6/2002 | Sun et al. | |
| 6,564,106 B2 * | 5/2003 | Guck et al. | 607/116 |
| 6,725,093 B1 | 4/2004 | Ben-Haim et al. | 607/9 |
| 2001/0034487 A1 * | 10/2001 | Cao et al. | 600/508 |
| 2004/0171959 A1 * | 9/2004 | Stadler et al. | 600/518 |
| 2004/0172067 A1 * | 9/2004 | Saba | 607/4 |
| 2005/0159781 A1 * | 7/2005 | Hsu | 607/4 |

FOREIGN PATENT DOCUMENTS

| | | |
|---|---|---|
| WO | WO 95/28988 A1 | 11/1995 |

* cited by examiner

METHOD FOR ELIMINATION OF VENTRICULAR PRO-ARRHYTHMIC EFFECT CAUSED BY ATRIAL THERAPY

FIELD OF THE INVENTION

The present invention relates generally to implantable medical devices and more specifically to an implantable cardioverter defibrillator system and method for controlling the delivery of atrial anti-tachycardia pacing therapies.

BACKGROUND OF THE INVENTION

In the past, atrial arrhythmias have been largely undertreated due to the perception that these arrhythmias are relatively benign. As more serious consequences of persistent atrial fibrillation have come to be understood, such as an associated risk of relatively more serious ventricular arrhythmias and stroke, there is a greater interest in providing implantable atrial or dual chamber cardioverter defibrillators for treating atrial arrhythmias.

Atrial arrhythmias, including atrial tachycardia (AT) and atrial fibrillation (AF) may be treated by either anti-tachycardia pacing therapies or high-voltage cardioversion/defibrillation shocks, or both. The high-voltage cardioversion/defibrillation shocks can be very painful to the patient. Since anti-tachycardia pacing (ATP) therapies are typically not perceived by the patient and generally consume less battery charge than high-voltage therapies, ATP therapies are typically attempted first in terminating an atrial arrhythmia. If the first ATP therapy delivered is not successful in terminating the atrial arrhythmia, a sequence of ATP therapies may be attempted. Since atrial arrhythmias are not directly life-threatening, delays in converting an atrial arrhythmia due to failed ATP therapies is tolerable. ATP therapies generally employ high rate pacing pulses or pulse bursts in an attempt to "overdrive" pace the heart such that re-entrant pathways sustaining an arrhythmia are interrupted.

Anti-tachycardia pacemakers are generally disclosed in U.S. Pat. No. 4,511,633 issued to Berkovits et al., U.S. Pat. No. 4,587,970 issued to Holley et al., U.S. Pat. No. 4,880,005 issued to Pless et al., and U.S. Pat. No. 4,726,380 issued to Vollmann et al., and U.S. Pat. No. 6,400,986 issued to Sun et al. Systems for delivering anti-tachycardia pacing pulses for treating atrial fibrillation are generally disclosed in PCT Publication No. WO95/28988 issued to Mongeon et al., and in PCT Publication No. WO95/28987 issued to Combs et al.

One risk associated with delivering atrial ATP therapies is that ventricular arrhythmias may be induced during or soon after ATP delivery. This pro-arrhythmic effect of atrial ATP therapies on the ventricle occurs when atrial pacing pulses are rapidly conducted to the ventricles thereby inducing ventricular arrhythmia. Ventricular pro-arrhythmia due to atrial ATP may also occur if the atrial pacing pulses capture the ventricular tissue inadvertently, due to a poorly placed or dislodged atrial pacing lead. It is highly undesirable to induce a more serious ventricular arrhythmia in the process of treating a less serious atrial arrhythmia. Typically, if a ventricular arrhythmia, including ventricular tachycardia or ventricular fibrillation, is detected immediately following an ATP therapy, the atrial arrhythmia therapies are disabled, even if the atrial arrhythmia is still present, so that the more serious ventricular arrhythmia can be treated.

Currently, ICDs control arrhythmia therapy delivery based on the type of arrhythmia detected independent of the rhythm of the opposite chamber. Detection of ventricular arrhythmias generally takes precedence over the detection of atrial arrhythmias because of the more serious nature of ventricular arrhythmias. Reference is made, for example, to U.S. Pat. No. 5,545,186 issued to Olson et al., which generally discloses a prioritized rule-based algorithm for arrhythmia detection, incorporated herein by reference in its entirety. Such prioritized arrhythmia detection has important advantages in detecting and treating the most lethal forms of arrhythmias first. For example, once a ventricular arrhythmia has been diagnosed by review of both atrial and ventricular information, therapies are delivered for treatment of the ventricular arrhythmia independent of the atrial rhythm at the time. If, however, an atrial arrhythmia is detected and an atrial ATP therapy is needed, the ATP therapy is delivered independent of the ventricular rhythm unless a ventricular arrhythmia is detected subsequent to an ATP therapy.

From the above discussion, however, it is apparent that it is desirable to avoid the ventricular pro-arrhythmic effects when delivering atrial ATP therapies. A need remains, therefore, for a method for controlling the delivery of atrial ATP therapies that includes monitoring the ventricular rhythm for pro-arrhythmic effects. Such a method preferably allows atrial ATP therapies to be disabled or aborted when ventricular pro-arrhythmia is evident in order to avoid inducing a ventricular arrhythmia as a result of treating an atrial arrhythmia.

SUMMARY OF THE INVENTION

The present invention provides an implantable cardioverter defibrillator system and method for controlling the delivery of atrial ATP therapies based on monitoring ventricular-related signals for pro-arrhythmic changes during and immediately after an atrial ATP therapy. The system preferably includes a dual chamber cardiac stimulation device and associated set of leads for sensing atrial and ventricular EGM signals, detecting atrial and ventricular arrhythmias, and delivering atrial and ventricular arrhythmia therapies including atrial ATP therapies. The system may alternatively employ leadless electrode systems for sensing cardiac depolarizations, such as electrical sensing via subcutaneous electrodes placed on the housing of the cardiac stimulation device. In another embodiment, the system may employ mechanical sensing of cardiac activity in lieu of a leads for sensing electrical cardiac activity. The device includes control circuitry for controlling sensing, arrhythmia detection, and arrhythmia therapy delivery operations, including controlling atrial ATP therapy delivery according to methods provided by the present invention.

The method for controlling atrial ATP therapy delivery includes monitoring ventricular activity during and immediately after ATP therapy for evidence of ventricular pro-arrhythmia. In one embodiment, evidence of ventricular pro-arrhythmia is based on ventricular rate acceleration. If a median R-R interval measured from an EGM or subcutaneous ECG signal becomes shorter than a predetermined reference R-R interval less an acceleration interval, pro-arrhythmia is detected. In an alternative embodiment, P-R intervals measured from EGM or subcutaneous ECG signals are monitored during and immediately after ATP therapy delivery to determine if a 1:1 conduction pattern between the atrium and ventricle exists as evidence of ventricular pro-arrhythmia. If a 1:1 or nearly 1:1 conduction pattern persists above a predetermined maximum ventricular rate, ventricular pro-arrhythmia is detected.

In yet another embodiment, ventricular pro-arrhythmia detection is based on R-wave morphology changes. If the R-wave morphology during or immediately after ATP therapy is substantially different than a pre-atrial ATP reference morphology, or substantially equal to a reference pro-arrhythmia morphology, ventricular pro-arrhythmia is detected. R-wave morphology may be evaluated from an intracardiac ventricular EGM, a far-field EGM, or a subcutaneous ECG.

If ventricular pro-arrhythmia is detected, the current atrial ATP therapy is aborted, and all subsequent ATP therapies scheduled for responding to the currently detected atrial arrhythmia are preferably disabled. Scheduled ATP therapies may be temporarily disabled for a predetermined period of time or until re-enabling conditions are satisfied, after which scheduled ATP therapy delivery will be attempted again as needed, with simultaneous ventricular pro-arrhythmia monitoring. The reason for aborting an atrial ATP therapy is stored in device memory with a time and date label. A record of ventricular pro-arrhythmia detections with associated atrial ATP therapies provides a physician with useful information in assessing atrial-ventricular interactions, patient pro-arrhythmia status, and therapy responses.

In one embodiment, all atrial ATP therapies are permanently disabled if atrial ATP therapies have been disabled in response to a predetermined number of ventricular pro-arrhythmia detections. Permanently disabled ATP therapies may be re-enabled by a clinician during a future device interrogation/programming session.

Methods included in the present invention for monitoring for ventricular pro-arrhythmia during atrial ATP may additionally or alternatively be embodied in an external device programmer. Application of atrial ATP therapies and monitoring for ventricular pro-arrhythmia at the time of device implant or at later clinical follow-up visits using algorithms implemented in an external programmer may be used for stratifying the risk of pro-arrhythmia to different atrial ATP therapies under rest and/or stress-induced conditions.

DETAILED DESCRIPTION OF THE INVENTION

Figure 1A:
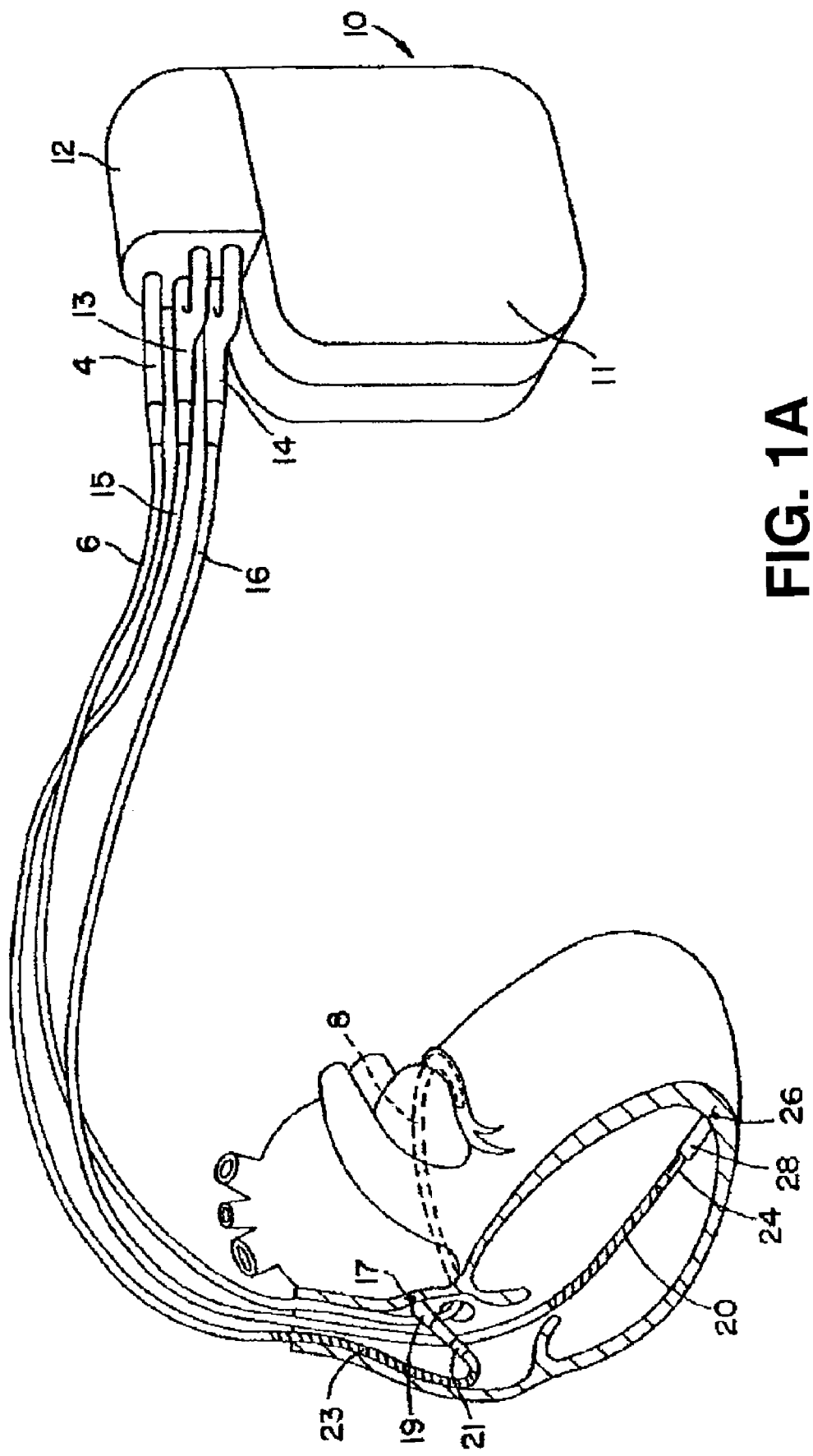
FIG. 1A is an illustration of an exemplary implantable cardiac stimulation device coupled to a set of leads implanted in a patient's heart.

FIG. 1A is an illustration of an exemplary implantable medical device in which the present invention may be practiced. Device 10 is coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers.

In FIG. 1A, the right ventricular lead 16 is positioned such that its distal end is in the right ventricle (RV) for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and RV coil electrode 20, each of which are connected to an insulated conductor contained within the body of lead 16. The proximal end of the insulated conductors are coupled to corresponding connectors carried by bifurcated connector 14 at the proximal end of lead 16 for providing electrical connection to the device 10.

The right atrial lead 15 is positioned such that its distal end is in the vicinity of the right atrium and the superior vena cava (SVC). Lead 15 is equipped with a ring electrode 21 and an extendable helix electrode 17, mounted retractably within electrode head 19, for sensing and pacing in the right atrium. Lead 15 is further equipped with an SVC coil electrode 23 for delivering high-energy shock therapy. The ring electrode 21, the helix electrode 17 and the SVC coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1A as having a defibrillation coil electrode 8 that may be used in combination with either the RV coil electrode 20 or the SVC coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 8, 20 or 23 for defibrillation of the atria or ventricles.

It is recognized that alternate lead systems may be substituted for the three lead system illustrated in FIG. 1A. For example, a lead system may include integrated bipolar leads or other types of transvenous leads, epicardial leads, subcutaneous leads, and so forth. While a particular multi-chamber cardiac stimulation device and lead system is illustrated in FIG. 1A, methodologies included in the present invention may be adapted for use with other atrial, dual chamber, or multichamber systems for delivering cardiac stimulation therapies.

The implementation of the present invention may also include a device that does not employ pacing leads as described here to detect and treat arrhythmias. For example, a device implanted subcutaneously or sub-muscularly in a position over the heart such as an auxiliary location could use non-intracardiac lead based methods of electrical sensing to detect and deliver therapy.

Figure 1B:
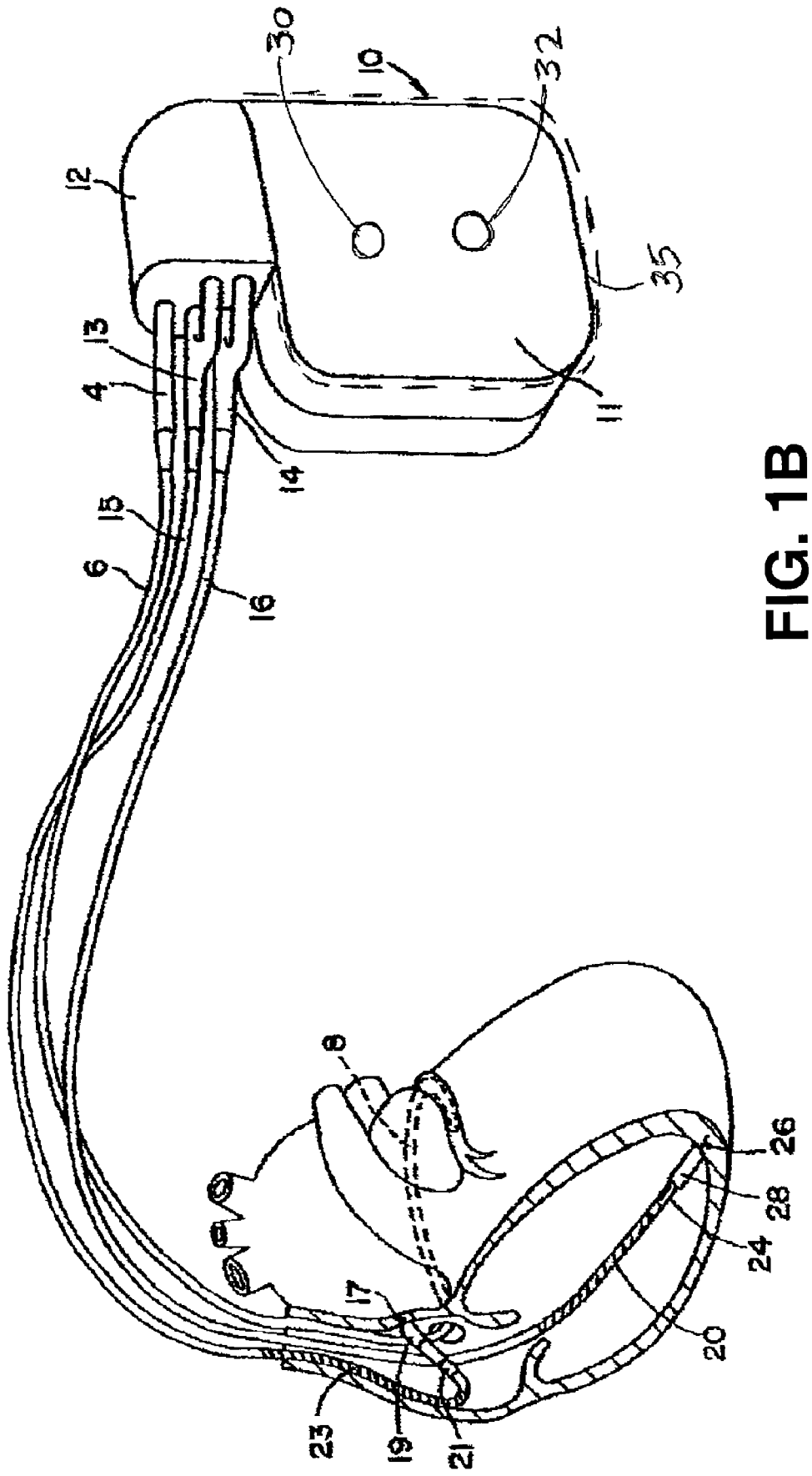
FIG. 1B is an illustration of an alternative cardiac stimulation device that includes subcutaneous ECG electrodes.

FIG. 1B is an illustration of an alternative embodiment of an implantable cardiac stimulation device in which the present invention may be practiced. In FIG. 1B, at least a portion of device housing 11 is provided with an insulative coating 35 with openings 30 and 32. The uninsulated openings 30 and 32 serve as subcutaneous electrodes for sensing ECG signals, which may be used, in accordance with the present invention, in monitoring a ventricular rhythm or R-wave morphology for signs of proarrhythmia. An implantable system having electrodes for subcutanteous measurement of an ECG is generally disclosed in commonly assigned U.S. Pat. No. 5,987,352 issued to Klein, incorporated herein by reference in its entirety. In alternative embodiments, multiple subcutaneous electrodes incorporated on the device housing 11 or positioned on subcutaneous leads extending from device 10 may be used to achieve multi-electrode ECG sensing. Multi-electrode ECG sensing in an implantable monitor is described in U.S. Pat. No. 5,313,953 issued to Yomtov, et al., incorporated herein by reference in its entirety.

Figure 2:
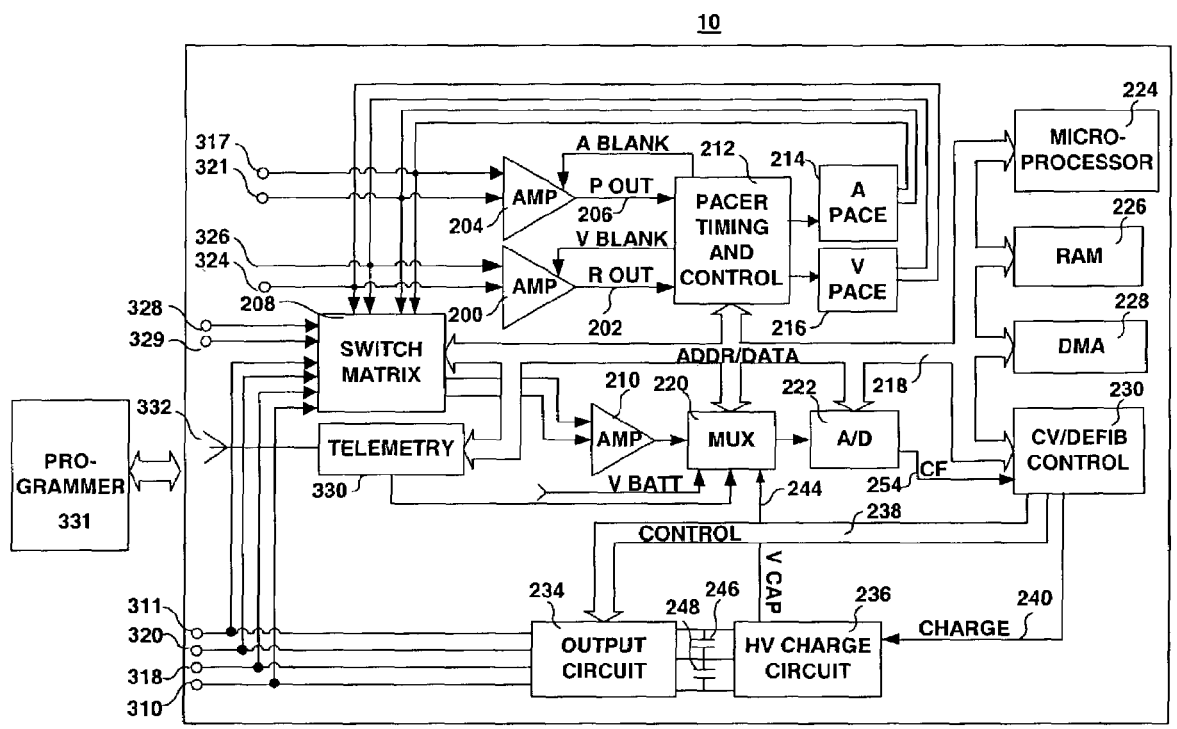
FIG. 2 is a functional block diagram of an implantable cardiac stimulation device in which the present invention may usefully be practiced.

FIG. 2 is a functional block diagram of a cardiac stimulation device in which the present invention may usefully be practiced. This diagram should be taken as exemplary of the type of device with which the invention may be embodied and not as limiting, as it is believed that the invention may usefully be practiced in a wide variety of device implementations, including devices providing therapies for treating only atrial arrhythmias, devices which do not include bradycardia pacing or devices which do not include defibrillation therapies. Thus, aspects of the present invention may be implemented in an atrial, dual-chamber or multi-chamber device that at least provides atrial anti-tachycardia pacing therapies and may additionally provide other pacing therapies, such as bradycardia pacing or cardiac resynchronization therapies, and/or higher-voltage cardioversion and/or defibrillation therapies. Methods described herein are preferably included in a dual chamber cardiac stimulation device that includes both ATP therapies and higher-voltage cardioversion/defibrillation therapies for treating both atrial and ventricular arrhythmias. The disclosed embodiment shown in FIG. 2 is a microprocessor-controlled device, but the methods of the present invention may also be practiced with devices employing dedicated digital circuitry for controlling some device functions.

With regard to the electrode system illustrated in FIG. 1B, device 10 is provided with a number of connection terminals for achieving electrical connection to the cardiac leads 6, 15, and 16 and their respective electrodes and subcutaneous electrodes 30 and 32. The connection terminal 311 provides electrical connection to the housing 11 for use as the indifferent electrode during unipolar stimulation or sensing. The connection terminals 328 and 329 provide connection to the subcutaneous electrodes 30 and 32 incorporated in housing 11, for use in sensing ECG signals. The connection terminals 320, 310, and 318 provide electrical connection to coil electrodes 20, 8 and 23 respectively. Each of connection terminals 311, 320, 310, 318, 328 and 329 are coupled to switch matrix 208 to allow selective sensing of integrated bipolar EGM signals or subcutaneous ECG signals for use in monitoring for ventricular proarrhythmia in accordance with the present invention. Each of connection terminals 311, 320, 310, and 318 are additionally coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals. Connection terminals 317, 321, 326, and 324 are also coupled to switch matrix 208 for selectively sensing intracardiac bipolar or unipolar EGM signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of device 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methods known in the art. In one embodiment of the present invention, digital signal analysis is performed on ventricular EGM and/or subcutaneous ECG signals for detecting ventricular proarrhythmia. The detected ventricular proarrhythmias are stored by microprocessor in random access memory 226.

The telemetry circuit 330 receives downlink telemetry from and sends uplink telemetry to an external programmer 331, as is conventional in implantable anti-arrhythmia devices, by means of an antenna 332. Received telemetry from external programmer 331 is provided to microprocessor 224 via multiplexer 220. Data to be uplinked to programmer 331 and control signals for the telemetry circuit 330 are provided by microprocessor 224 via address/data bus 218. Numerous types of telemetry systems known for use in implantable devices may be used.

The remainder of circuitry illustrated in FIG. 2 is dedicated to the provision of cardiac pacing, cardioversion and defibrillation therapies and, for the purposes of the present invention, may correspond to circuitry known in the prior art. In the exemplary embodiment shown in FIG. 2, the pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals, P-P intervals, P-R intervals, and R-P intervals, which measures are stored in memory 226 and used to diagnose the occurrence of a variety of arrhythmias. In accordance with the present invention, stored intervals may be used in evaluating the ventricular response to atrial ATP therapies to detect interval changes indicative of ventricular pro-arrhythmia.

Microprocessor 224 operates as an interrupt driven device and is responsive to interrupts from pacer timing and control circuitry 212 corresponding to the occurrences of sensed P-waves and R-waves and corresponding to the generation of cardiac pacing pulses. Any necessary mathematical calculations to be performed by microprocessor 224 and any updating of the values or intervals controlled by pacer timing/control circuitry 212 take place following such interrupts. A portion of the random access memory 226 may be configured as a number of recirculating buffers capable of holding a series of measured intervals, which may be analyzed in response to a pace or sense interrupt by microprocessor 224 for diagnosing an arrhythmia, and, in accordance with the present invention, detecting ventricular pro-arrhythmic changes during atrial ATP therapies.

The present invention may employ any arrhythmia detection algorithm known in the art to detect the occurrence of arrhythmias. For example, the detection methods disclosed in the above-cited U.S. Pat. No. 5,545,186 issued to Olson et al., and in U.S. Pat. No. 5,755,736 issued to Gillberg et al., also incorporated herein by reference in its entirety, for the detection of atrial fibrillation and tachycardias may be employed. Alternatively, other known detection algorithms for use in conjunction with implantable cardioverter defibrillators, such as those disclosed in U.S. Pat. No. 5,161,527 issued to Nappholz et al, U.S. Pat. No. 5,720,295 issued to Greenhut et al., or U.S. Pat. No. 5,107,850 issued to Olive, all incorporated by reference in their entireties, may also be employed.

A device embodying the present invention may also include the ability to treat ventricular tachyarrhythmias, as discussed above. In the event such capability is desired, any of the prior art ventricular tachyarrhythmia detection methods may be employed, including those in the above-cited Olson patent and Gillberg et al. patent, as well as the detection methods disclosed in U.S. Pat. No. 5,620,471 issued to Duncan, U.S. Pat. No. 4,880,005 issued to Pless et al., and U.S. Pat. No. 5,560,369 issued to McClure et al., all incorporated by reference in their entireties.

In addition, the device may be configured such that the patient initiates delivery of the therapy by means of an external controller, such that the device may not employ a detection method of its own as a prerequisite to a delivery of therapy. In this context, a patient activator as disclosed in U.S. Pat. No. 5,755,737, issued to Prieve et al, incorporated by reference in its entirety herein, may be employed. The particular choice of patient activator is not critical to the success of the invention, and any workable method for initiating the delivery of an atrial therapy may usefully be employed.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in the above-cited U.S. Pat. No. 4,880,005, issued to Pless et al., U.S. Pat. No. 4,577,633, issued to Berkovits et al., U.S. Pat. No. 4,726,380, issued to Vollmann et al., and U.S. Pat. No. 4,587,970, issued to Holley et al., all of which are incorporated herein by reference in their entireties may also be used.

In the event that generation of a cardioversion or defibrillation pulse is required, microprocessor 224 employs the escape interval counter to control timing of such cardioversion and defibrillation shocks, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212.

One embodiment of an appropriate system for delivery and synchronization of ventricular cardioversion and defibrillation shocks and for controlling the timing functions related to them is disclosed in more detail in commonly assigned U.S. Pat. No. 5,188,105 by Keimel, incorporated herein by reference in its entirety. Any known ventricular cardioversion or defibrillation pulse control circuitry is believed usable in conjunction with the present invention. For example, circuitry controlling the timing and generation of cardioversion and defibrillation shocks as disclosed in U.S. Pat. No. 4,384,585, issued to Zipes on May 24, 1983, in U.S. Pat. No. 4,949,719 issued to Pless et al, and in U.S. Pat. No. 4,375,817, issued to Engle et al, all incorporated herein by reference in their entireties may also be employed. In addition, high frequency pulse bursts may be delivered to electrode terminals 317 and 321 to terminate atrial tachyarrhythmias, as described in the above-cited PCT Patent Publication No. WO95/28987, filed by Combs et al., and PCT Patent Publication No. WO95/28988, filed by Mongeon et al., both incorporated herein by reference in their entireties. When the term "anti-tachycardia pacing" (ATP) is used henceforth, it will be assumed to include high frequency burst therapy.

In the illustrated device, delivery of cardioversion or defibrillation shocks is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

In modern implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion shocks if the rate of the detected tachycardia is above a preset threshold. The references cited above in conjunction with descriptions of prior art tachycardia detection and treatment therapies are applicable here as well.

In the event that atrial fibrillation is identified, atrial anti-tachycardia pacing may be employed as the initial attempted therapy. Subsequent therapies may be delivery of high amplitude defibrillation shocks, typically in excess of 5 joules. Lower energy levels may be employed for cardioversion. As in the case of currently available ICDs, and as discussed in the above-cited references, it is envisioned that the amplitude of the defibrillation shock may be incremented in response to failure of an initial shock or shocks to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,726,380, issued to Vollmann et al. and U.S. Pat. No. 4,587,970, issued to Holley et al.

Figure 3:
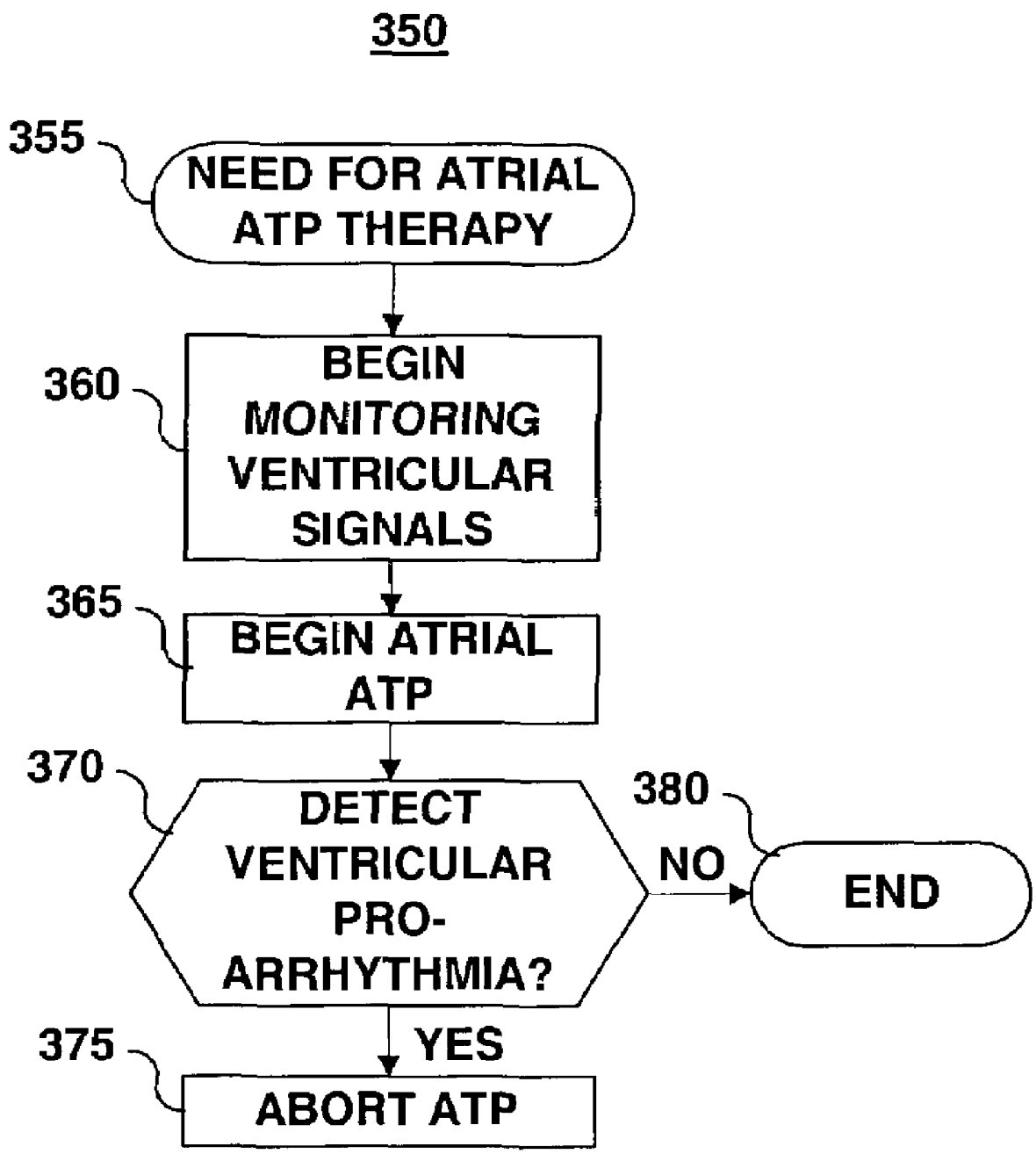
FIG. 3 is a flow chart of a method for controlling the delivery of atrial ATP therapies according to the present invention.

FIG. 3 is a flow chart of a method for controlling the delivery of atrial ATP therapies according to the present invention. Atrial ATP therapies may include, but are not limited to, ramp ATP, burst ATP, and high frequency burst therapies. During ramp ATP therapies, one or more atrial pacing sequences are delivered with decreasing pacing pulse intervals within a sequence. Burst ATP therapies typically include a number of pulses at a fixed rate. High frequency burst is similar, but with a very rapid series of pulses, typically 20-60 Hz, of programmable duration. A variation of a burst ATP therapy includes one or more bursts each followed by one or more premature pacing pulses.

Method 350 is initiated when the device determines that a need for atrial ATP therapy exists. A need for atrial ATP therapy typically arises upon AT or AF detection when at least one automatic ATP therapy is programmed to be included in a menu of AT or AF therapies. The need for atrial ATP therapy may alternatively be the result of a patient-initiated therapy trigger. The need for atrial ATP therapy may alternatively be the result of a physician-initiated atrial ATP therapy delivered for evaluating the ventricular response to atrial ATP. At step 360, monitoring of ventricular signals begins, and at step 365, the scheduled atrial ATP sequence begins.

As will be described in greater detail below, monitoring of ventricular signals may begin prior to starting an ATP sequence such that one or more reference values associated with the ventricular activity prior to any pro-arrhythmic changes may be obtained. In alternative embodiments, pre-determined reference values are stored or programmed into the device in advance, and ventricular monitoring begins simultaneously with the delivery of a scheduled ATP sequence.

Once the ATP sequence is initiated, a determination is made as to whether evidence of ventricular pro-arrhythmia is detected. Ventricular monitoring continues throughout an ATP sequence and may additionally continue for a predetermined period of time or number of cardiac cycles after completion of an ATP sequence in order to detect evidence of ventricular pro-arrhythmia effects of the ATP therapy during and immediately after atrial ATP. As will be described in greater detail below, ventricular pro-arrhythmia may be detected based on changes in the ventricular rate, R-wave morphology, and/or atrial-ventricular conduction patterns, or any method known in the art for identifying ventricular arrhythmia precursors.

Ventricular rate changes may be determined by sensing R-R intervals from an EGM or ECG signal. Alternatively ventricular rate changes may be derived from other ventricular activity-related signals received from other sensors of cardiac activity, such as, but not limited to, ventricular or arterial blood pressure, ventricular wall motion, thoracic impedance, heart sounds, or blood flow.

If ventricular pro-arrhythmic changes are not detected at decision step 370 during or soon after the delivery of atrial ATP, method 350 is concluded at termination step 380. If ventricular pro-arrhythmic changes are detected, the current ATP sequence is immediately aborted at step 375.

While method 350 of FIG. 3 has been described in the context of an implantable cardiac stimulation device embodiment, it is contemplated that methods described herein may be implemented in an external programmer in communication with an implanted device for use at the time of device implant or at later clinical follow-up visits to evaluate the pro-arrhythmic state of the patient and the ventricular response to different atrial ATP-therapies. The risk of ventricular pro-arrhythmia to different atrial ATP therapies may be stratified, and this information may be used by a physician in programming AT/AF therapies. Aspects of the present invention may also be embodied in an external programmer and external cardioverter/defibrillator system used for diagnostic purposes to assess a patient's atrial and ventricular responses to atrial ATP therapies. Methods for assessing pro-arrhythmia risk may be applied during exercise or drug-induced stress testing to provide additional information regarding the pro-arrhythmia status of the patient.

Figure 4A:
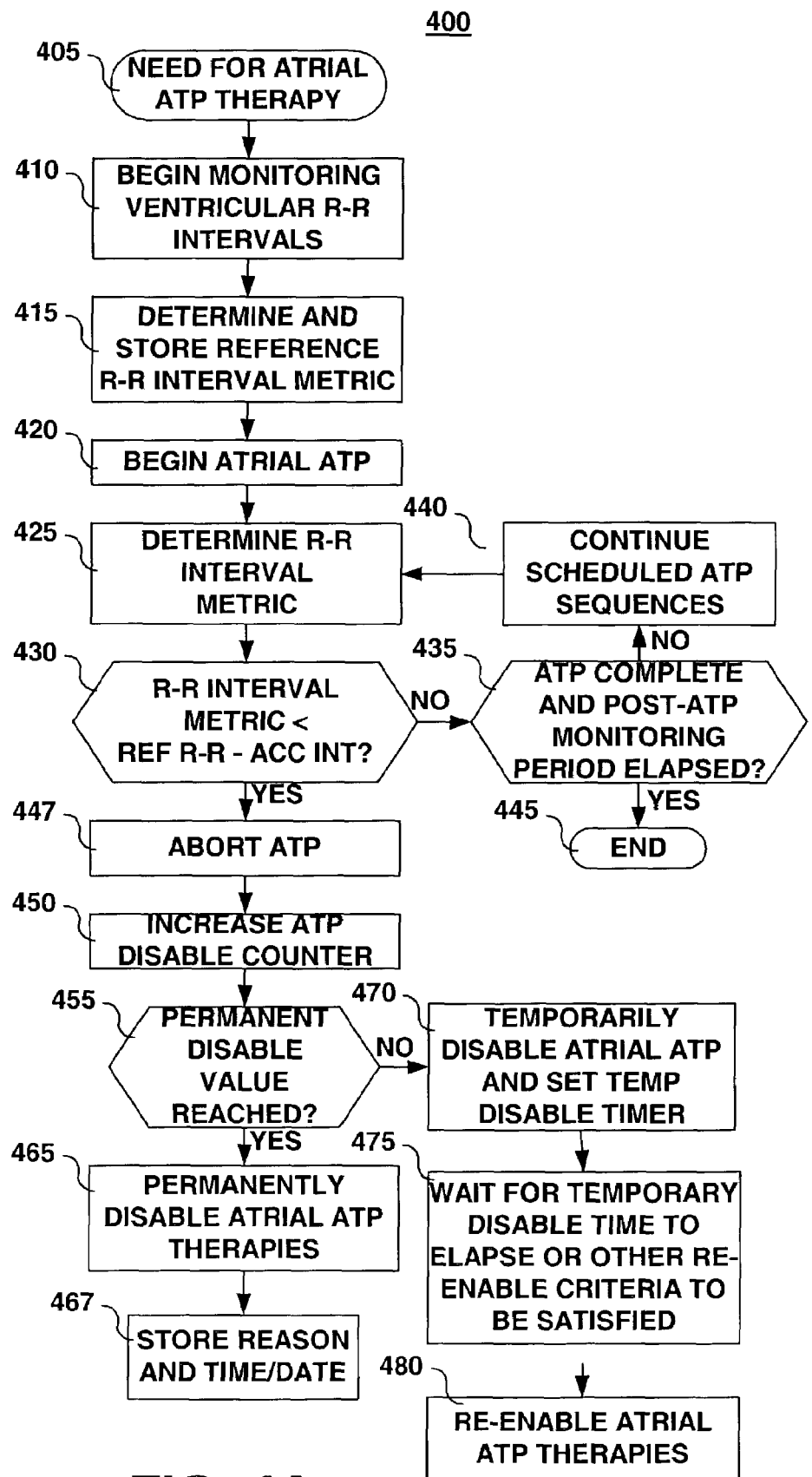
FIG. 4A is a flow chart of a method for controlling atrial ATP therapy delivery based on pro-arrhythmic changes in the ventricular rate according to an embodiment of the present invention.

FIG. 4A is a flow chart of a method according to an embodiment of the present invention for controlling atrial ATP therapy delivery based on pro-arrhythmic changes in the ventricular rate. Acceleration of the ventricular rate during atrial ATP may be the result of rapid conduction of the atrial ATP pulses to the ventricles, which could lead to ventricular arrhythmia. Method 400 begins upon determination of a need for atrial ATP therapy at initiation step 405. At step 410, monitoring of the ventricular R-R intervals begins. At step 415 a reference R-R interval metric is determined and stored. The reference R-R interval metric may be determined based on a given number of R-R intervals stored in a recirculating buffer of device memory at the time that AT or AF detection is made or a patient-initiated therapy is triggered. Alternatively, a given number of R-R intervals may be measured at the start of R-R interval monitoring at step 410 for use in determining a reference R-R interval metric.

The reference R-R interval metric is a representative R-R cycle length to which comparisons will be made to detect ventricular rate acceleration due to rapid conduction of atrial ATP pulses to the ventricle. The reference R-R interval metric may be calculated in a number of ways based on pre-atrial ATP R-R intervals. For example, the reference R-R interval may be calculated as the mean or median of a given number of pre-atrial ATP R-R intervals, the minimum R-R interval out of a given number of pre-atrial ATP R-R intervals, or the minimum running mean or median R-R interval out of a given number of pre-atrial ATP R-R intervals. In an alternative embodiment, the reference R-R interval is a pre-set interval, which may be a programmable or fixed interval, stored in device memory.

At step 420, atrial ATP begins. At step 425, an R-R interval metric during atrial ATP is determined. The R-R interval metric is calculated based on R-R intervals measured starting from the onset of atrial ATP and may be calculated in the same way or differently than the R-R reference interval metric. The R-R interval metric during atrial ATP, for example, may be equal to the current R-R interval, calculated as a running mean/median value of a given number of consecutive R-R intervals, or the minimum R-R interval out of a given number of consecutive R-R intervals, etc.

At decision step 430, the R-R interval metric is compared to the reference R-R interval metric. Ventricular rate acceleration is detected as evidence of ventricular pro-arrhythmia if a measured or calculated R-R interval metric during or soon after atrial ATP is less than the reference R-R interval metric by a predetermined acceleration interval (ACC INT). The acceleration interval may be a fixed or programmable value or may be based on a percentage of the reference R-R interval metric.

If the result of the comparison made at step 430 is negative, ventricular pro-arrhythmia is not detected. Method 400 proceeds to step 435 to determine if the entire ATP therapy sequence has been completed and if a post-ATP monitoring period has elapsed. If not, delivery of scheduled ATP sequences continues as needed (until AT/AF is terminated) at step 440. Scheduled ATP therapies may include multiple sequences of multiple ATP therapies. As long as AT/AF is being detected and atrial ATP is being delivered, continuous monitoring of the ventricular rate is performed by method 400 by returning to step 425 for determining the next R-R interval metric. R-R interval monitoring may continue for a predetermined period of time or number of ventricular cycles after the ATP therapy is completed. After a post-ATP monitoring period has elapsed, which may be determined based on a timer or ventricular event counter, with no occurrence of ventricular pro-arrhythmia detection, method 400 is terminated at step 445. The atrial ATP therapy has been delivered without pro-arrhythmic effects.

If, however, at any time during atrial ATP or during a post-atrial ATP monitoring period, ventricular pro-arrhythmia is detected based on comparing a measured R-R interval metric to a reference R-R interval metric at decision step 430, the current atrial ATP therapy is immediately aborted at step 447. Upon aborting an ATP therapy, an atrial ATP disable counter is increased by one at step 450. The atrial ATP disable counter is used to count the number of times atrial ATP is aborted due to positive detection of ventricular pro-arrhythmia changes. The disable counter has been previously initialized to 0 when the ventricular pro-arrhythmia monitoring feature is first enabled by a physician (not shown in FIG. 4A).

At decision step 455, the disable counter value is compared to a permanent disable value. The permanent disable value may be a fixed or programmable number corresponding to the number of times atrial ATP therapies may be aborted before permanently disabling ATP therapies. A permanent disable value may be, for example, on the order of 1 to 5. If a permanent disable value is reached, atrial ATP therapies are permanently disabled at step 465. Time and date information and the reason for permanently disabling the ATP therapies are stored at step 467. A physician may review this information along with a record of AT/AF detections and delivered and aborted atrial ATP therapies at a future device interrogation session. Atrial ATP therapies may be re-enabled by the physician upon which the atrial ATP disable counter is re-initialized to 0. The physician may use the stored information in re-programming atrial ATP therapies such that ATP sequences observed to be pro-arrhythmic may be adjusted or removed from a programmed menu of AT/AF therapies. Stored data is also useful to a physician in evaluating the pro-arrhythmia status of the patient, assessing both the atrial and ventricular responses to an atrial ATP therapy, and may be useful in managing ventricular arrhythmia therapies and/or anti-arrhythmic medical therapies.

If the permanent disable value is not reached at decision step 455, ATP therapies are temporarily disabled at step 470. Thus, any remaining atrial ATP sequences scheduled for delivery in response to the current AT/AF detection or patient-initiated therapy trigger are temporarily disabled. A temporary disable timer is then set, and method 400 waits for the temporary disable time to elapse at step 475. In alternative embodiments, re-enabling criteria other than, or in addition to, expiration of a temporary disable time may be defined. For example, temporarily disabled atrial ATP therapies may be re-enabled at a specified time of day. Alternatively, atrial ATP therapies may be re-enabled based on the status of the ventricular rhythm. For example, temporarily disabled atrial ATP therapies may be re-enabled when the ventricular rate is below a predetermined maximum, within a specified range, meets predefined stability criteria, and/or other ventricular rhythm-related criteria.

At step 480, atrial ATP therapies are re-enabled. If AT/AF is still being detected, the ATP therapy sequence may resume, and method 400 will begin again at step 405. If the AT/AF episode has spontaneously terminated, atrial ATP therapies may be delivered in response to a future AT/AF detection (or patient-initiated therapy trigger) with method 400 being initiated upon determination of a need for atrial ATP. Temporarily disabling atrial ATP therapies and re-enabling them at a later time may allow atrial ATP therapies to be successfully delivered at a time when the patient is in a less pro-arrhythmic state.

Figure 4B:
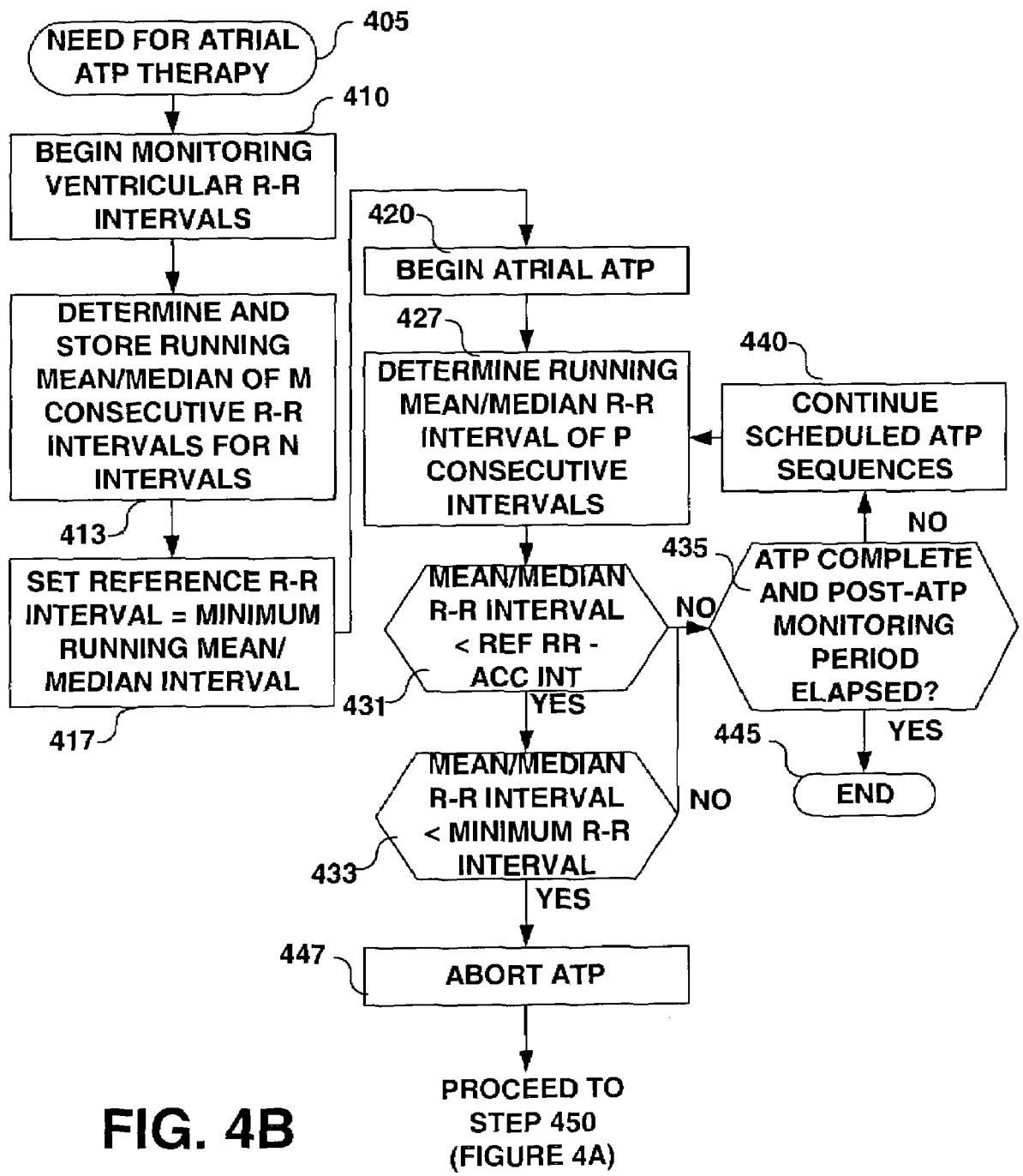
FIG. 4B is a flow chart providing more detailed steps included in a method for controlling atrial ATP therapy delivery based on pro-arrhythmic changes in the ventricular rate.

FIG. 4B is a flow chart of a method for controlling atrial ATP therapy delivery based on pro-arrhythmic changes in the ventricular rate according to the present invention. In FIG. 4B, steps included in method 401 correspond to identically labeled steps included in method 400 of FIG. 4A. However, in method 401, after beginning ventricular rate monitoring for pro-arrhythmic changes at step 410, steps for determining a reference R-R interval metric include: step 413 for determining and storing a running mean or median value of a given number of consecutive R-R intervals, M, for a predetermined number of R-R intervals, N; and step 417 for setting the reference R-R interval metric equal to the minimum mean or median value determined at step 413. In one embodiment, running mean or median values are determined from five consecutive R-R intervals for the 32 consecutive R-R intervals occurring prior to starting atrial ATP delivery. The reference R-R interval metric is set equal to the minimum running mean/median value.

Atrial ATP begins at step 420. At step 427, the R-R interval metric for detecting acceleration of the ventricular rate during atrial ATP is measured as the running mean or median of a given number of consecutive R-R intervals, P, for example 5 consecutive R-R intervals. The number of consecutive R-R intervals, P, used for calculating running mean or median values during atrial ATP may be equal to or different than the number of consecutive R-R intervals, M, used for calculating pre-atrial ATP running mean or median values. At step 431, the running mean or median R-R interval is compared to the reference R-R interval determined at step 417. If the running mean/median R-R interval is less than the reference R-R interval minus an acceleration interval (ACC INT), acceleration of the ventricular rate is detected as evidence of ventricular pro-arrhythmia. In this embodiment, an additional ventricular rate criterion for detecting ventricular pro-arrhythmia and aborting atrial ATP is applied at decision step 433. If the mean/median R-R interval is also less than a predetermined minimum R-R interval, as determined at decision step 433, atrial ATP is aborted at step 447. Method 401 proceeds to step 450 of FIG. 4A and steps 450 through 480 are performed as described above for temporarily or permanently disabling atrial ATP.

If the running mean/median R-R interval is not less than the reference R-R interval minus an acceleration interval, as determined at decision step 431, or if the mean/median R-R interval is not less than a minimum R-R interval as determined at decision step 433, method 401 proceeds to step 435. Atrial ATP and ventricular rate monitoring continue, as described previously in conjunction with FIG. 4A, until the scheduled atrial ATP sequences are completed (or AT/AF is terminated) and a post-atrial ATP monitoring period has elapsed or until ventricular pro-arrhythmia is detected based on the satisfaction of ventricular rate acceleration and ventricular rate criterion applied at steps 431 and 433.

While the methods shown in FIGS. 4A and 4B have been described with regard to ventricular rate and ventricular rate acceleration determinations made based on R-R intervals sensed from EGM or ECG signals, other cardiac-related signals from which ventricular rate and ventricular rate acceleration changes may be derived may alternatively be employed for detecting pro-arrhythmic ventricular rate changes, as noted previously.

Figure 5:
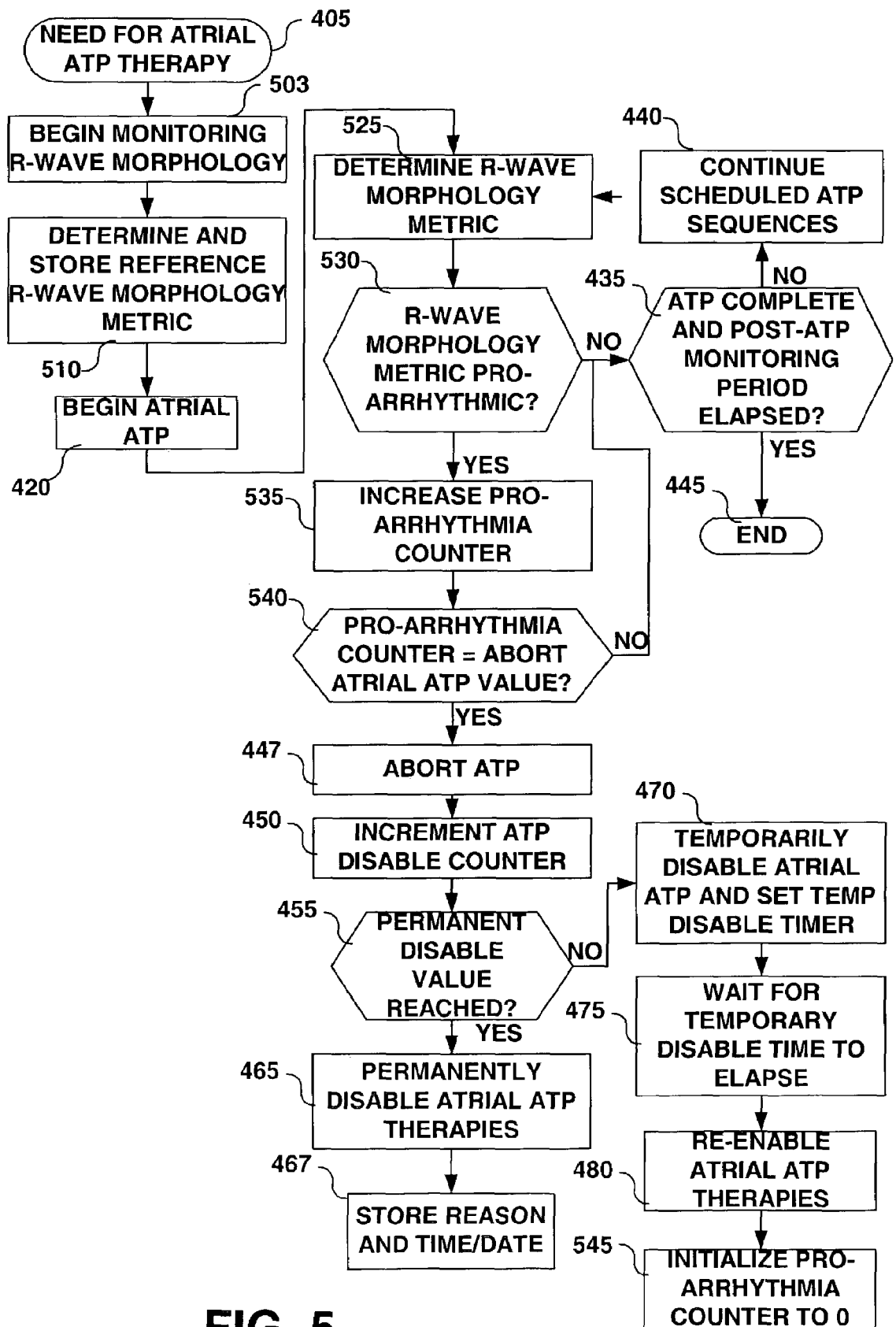
FIG. 5 is a flow chart of an alternative method for controlling atrial ATP therapy delivery based on pro-arrhythmic changes in R-wave morphology.

FIG. 5 is a flow chart of an alternative method for controlling atrial ATP therapy delivery based on pro-arrhythmic changes in R-wave morphology according to the present invention. In FIG. 5, steps included in method 500 correspond to identically labeled steps in method 400 of FIG. 4A. Like method 400, method 500 begins upon determining a need for atrial ATP therapy at step 405. However, rather than monitoring R-R intervals for the detection of pro-arrhythmic rate changes, monitoring of ventricular R-wave morphology begins at step 505 for the detection of pro-arrhythmic R-wave morphology changes. R-wave morphology may be measured from any pair of available electrodes (intracardiac or subcutaneous), which may be a different pair of electrodes than the electrodes used to determine R-R intervals.

At step 510, a pre-atrial ATP reference R-wave morphology metric is determined and stored. In one embodiment, an R-wave morphology metric is determined based on a predetermined number of digitized R-wave signals sensed prior to delivering atrial ATP. One or more R-wave morphology metrics may be determined from one or more digitized R-wave signals. An R-wave morphology metric may be, but is not limited to, an R-wave morphology template used for comparing to a sensed R-wave morphology and/or a QRS width measurement.

In an alternative embodiment, step 510 for determining and storing one or more reference R-wave morphology metrics associated with sinus R-waves may be performed under physician supervision. R-wave morphology metrics may be programmed by a physician according to known sinus R-wave characteristics for a particular patient, or one or more metrics may be determined automatically at a time when the patient is known to be in sinus rhythm. In yet another variation of this embodiment, R-wave morphology metrics relating to a known pro-arrhythmic R-wave morphology, rather than normal sinus R-wave morphology, may be determined and stored.

At step 420, atrial ATP begins. At step 525, one or more R-wave morphology metrics are determined from digitized R-wave signals received during atrial ATP for comparison to the reference R-wave morphology metric(s) at decision step 530. By comparing the R-wave morphology metric measured during atrial ATP to a reference R-wave morphology metric, the R-wave may be categorized as "pro-arrhythmic" or "normal". If a pro-arrhythmic R-wave is identified, a pro-arrhythmia counter is updated at step 535. The pro-arrhythmia counter is used to count the number of sensed R-waves during atrial ATP that appear to be pro-arrhythmic.

The value stored in the pro-arrhythmia counter is compared to an abort atrial ATP value at decision step 540. The abort atrial ATP value may be a fixed or programmable value which may be equal to or greater than 1. The abort atrial ATP value is the number of identified pro-arrhythmic R-waves required to detect ventricular pro-arrhythmia and abort atrial ATP. If the abort atrial ATP value is not reached, method 500 proceeds to step 435 to continue monitoring R-wave morphology during the remaining atrial ATP sequence(s) and any post-atrial ATP monitoring period.

If, however, the abort atrial ATP value is reached, as determined at decision step 540, method 500 immediately aborts the current ATP sequence at step 447. Steps 450 through 480 are performed as described previously in conjunction with FIG. 4A. After re-enabling temporarily disabled atrial ATP therapies at step 480, the pro-arrhythmia counter is re-set to an initial value of 0.

In one embodiment, the reference R-wave morphology determination performed at step 510 includes performing a wavelet transform of a digitized R-wave as generally disclosed in the U.S. Pat. No. 6,393,316 to Gillberg et al. Reference is also made to Koyrakh L., et al., "Wavelet transform based algorithms for EGM morphology discrimination of implantable ICDs," Computers in Cardiology. 2000;26:343-346. Alternative methods for comparing waveform morphologies which may be used in the present invention include using an area of distance or a correlation waveform analysis metric, as also described in the above-cited '316 patent to Gillberg.

The wavelet transform method is fundamentally based on "template matching", a mathematical comparison of a known template EGM signal to the EGM signal from an unknown rhythm. In accordance with the present invention, this comparison forms the basis for determining a pro-arrhythmic change in the R-wave morphology during atrial ATP.

Template acquisition may be performed either automatically or with physician supervision. Templates are preferably acquired on a patient-by-patient basis because of variability in EGM waveforms due to inter-individual variability and differences in the type and location of EGM sensing electrodes. Templates may be acquired during normal sinus rhythm or obtained from stored data associated with ventricular pro-arrhythmia or ventricular arrhythmias. A digitized EGM segment used for setting an R-wave template is preferably limited to the R-wave. A snippet of EGM data associated with the R-wave may be taken by centering a morphology window at each ventricular sensed event as generally described in the '316 patent to Gillberg. In this embodiment, the wavelet transform is performed on the EGM data segment at step 510 to determine a reference R-wave template.

The reference R-wave template may correspond to a normal sinus R-wave, a pro-arrhythmic R-wave, or a known arrhythmia R-wave. Alternatively, templates may be acquired corresponding to a normal and pro-arrhythmic and/or arrhythmic R-waves. At step 530, a digitized R-wave acquired during atrial ATP is compared to the one or more reference templates for categorizing the R-wave as normal, pro-arrhythmic, or arrhythmic depending on whether the digitized R-wave is substantially equal to or unequal to a given template. If the R-wave is categorized as pro-arrhythmic (or arrhythmic) based on this template comparison, the pro-arrhythmia counter is increased at step 535.

In another embodiment of the present invention, the morphological analysis for detecting ventricular pro-arrhythmia includes measuring the QRS width during atrial ATP and comparing the measured QRS width to a reference QRS width associated with normal sinus rhythm or pre-atrial ATP beats. The QRS width may then be used to classify the beat as a "normal" or "pro-arrhythmic" beat.

A preferred method for determining EGM width employed by the present invention is generally disclosed in U.S. Pat. No. 5,312,441 issued to Mader, et al., incorporated herein by reference in its entirety. Identification of the beginning and end points of an R-wave is accomplished by the occurrence of a series of sequential digitized signals which differ from preceding signals by more than or less than a predetermined amount. The width of the R-wave is defined as the interval between the identified beginning and end points. A reference QRS width may be predefined or measured during pre-atrial beats at step 510. The reference QRS width is used to discriminate between sinus R-waves, which are relatively narrow, and pro-arrhythmic R-waves, which may be wider than a sinus R-wave. In this embodiment, the QRS width for the currently sensed ventricular event, or a running average of QRS widths or other metric of QRS width during atrial ATP, is determined at step 525. The measured QRS width is compared to the reference QRS width at step 530. If the QRS width is determined as pro-arrhythmic based on this comparison, the pro-arrhythmic counter is increased at step 535.

In alternative embodiments, other methods known in the art, or methods to be developed in the future, for performing a morphological or other analysis of EGM features that reliably distinguishes a sinus QRS complex from a pro-arrhythmic QRS complex may be successfully used in the present invention.

Figure 6A:
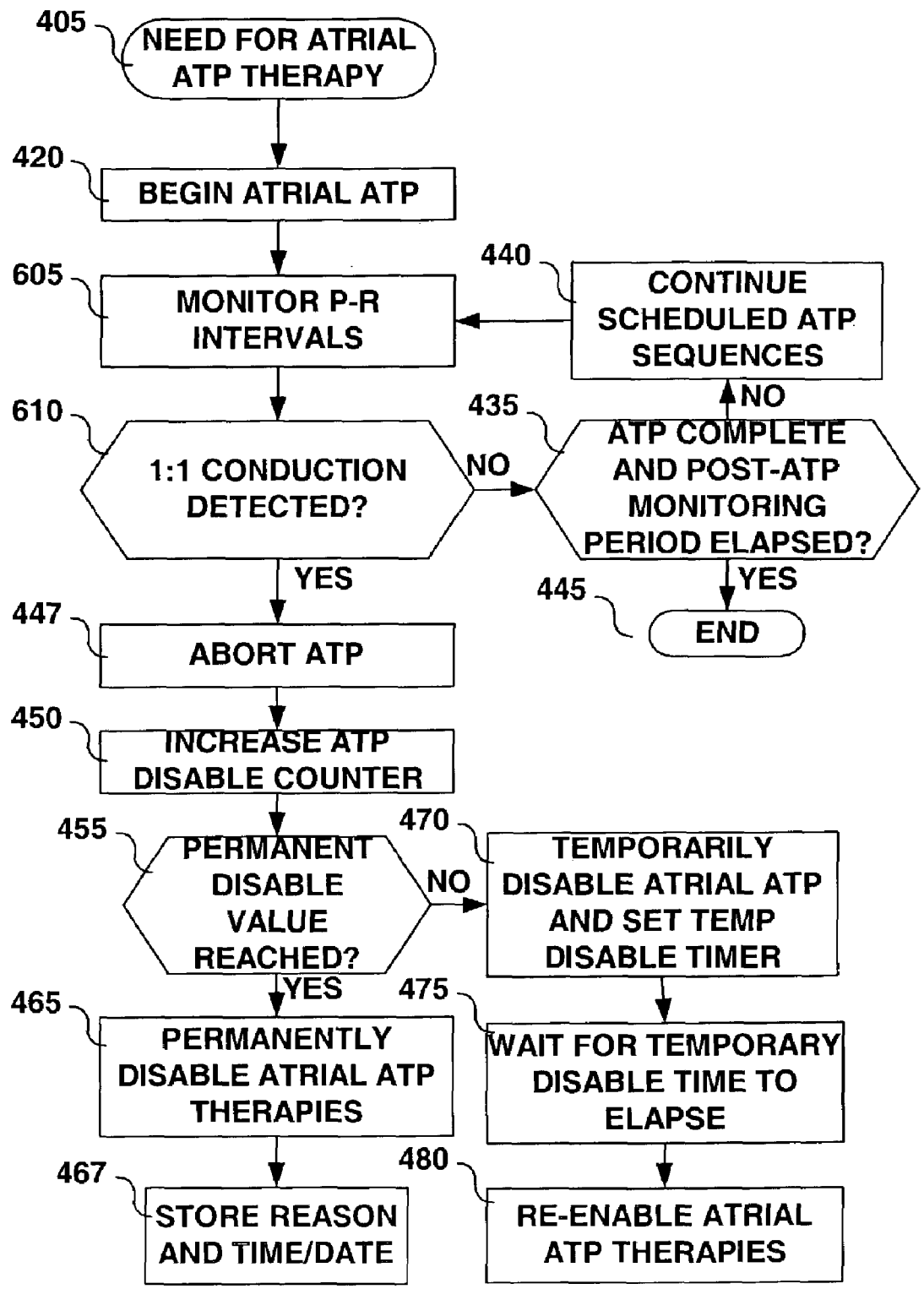
FIG. 6A is a flow chart of an alternative embodiment of the present invention for controlling atrial ATP delivery based on analyzing the atrial-ventricular conduction pattern for evidence of ventricular pro-arrhythmia.

FIG. 6A is a flow chart of an alternative embodiment of the present invention for controlling atrial ATP delivery based on analyzing the atrial-ventricular conduction pattern for evidence of ventricular pro-arrhythmia. Steps included in method 600 correspond to identically-numbered steps included in method 400 described previously in conjunction with FIG. 4A. However, in method 600, upon detecting the need for atrial ATP therapy at step 405, atrial ATP begins immediately at step 420. During atrial ATP, P-R intervals are monitored at step 605 for detecting a 1:1 or nearly 1:1 conduction pattern between the atria and the ventricles as evidence of ventricular pro-arrhythmia.

If 1:1 or nearly 1:1 conduction is not detected at decision step 610 based on the monitored P-R intervals, method 600 proceeds to step 435 to continue delivering scheduled atrial ATP sequences (as long as needed) and monitoring for 1:1 conduction patterns during atrial ATP and any post-atrial ATP monitoring period. If a 1:1 or nearly 1:1 conduction pattern is detected at decision step 610, the current atrial ATP sequence is immediately aborted at step 447. A 1:1 or nearly 1:1 conduction pattern during atrial ATP, persisting with increasing pacing rates, may induce a ventricular arrhythmia. Steps 450 through 480 are performed as described previously in conjunction with FIG. 4A.

Figure 6B:
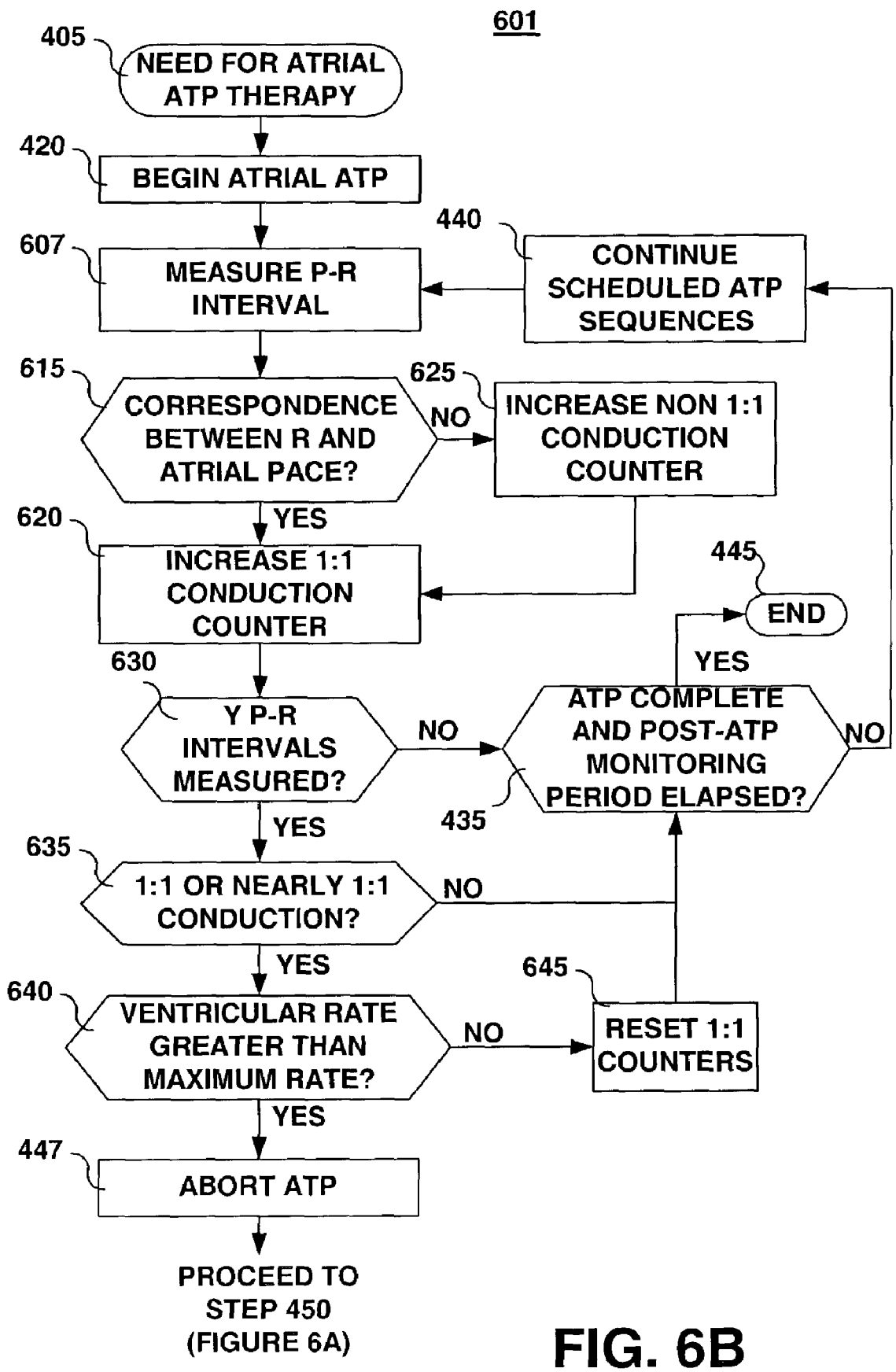
FIG. 6B is a flow chart summarizing more detailed steps included in a method for controlling atrial ATP delivery based on analyzing the atrial-ventricular conduction pattern for evidence of ventricular pro-arrhythmia.

FIG. 6B is a flow chart summarizing more detailed steps of a method for controlling atrial ATP delivery based on analyzing the atrial-ventricular conduction pattern for evidence of ventricular pro-arrhythmia according to the present invention. In FIG. 6B, steps included in method 601 correspond to identically-labeled steps included in method 600 of FIG. 6A. In method 601, steps for monitoring P-R intervals for detecting 1:1 conduction as evidence of ventricular pro-arrhythmia include step 607 through 640. At step 607, a P-R interval is measured as the interval between a sensed P-wave and a sensed R-wave. Alternatively, the P-R interval may be measured between an atrial pacing pulse and the immediately subsequent R-wave. At step 615, method 601 determines, based on P-R interval length, if the R-wave corresponds to or is associated with atrial activation (either an atrial P-wave or the atrial pace). In one embodiment, a sensed R-wave is determined to be associated with atrial activation at step 615 if the P-R interval is within a specified conduction interval range.

If the R-wave is not associated with atrial activation, as determined at decision step 615, a non-1:1 conduction counter is increased by one count at step 625. The non-1:1 conduction counter is used for counting R-waves that are not associated with atrial activation. If the R-wave is determined to be associated with atrial activation based on the measured P-R interval, a 1:1 conduction counter is increased by one at step 620. The 1:1 conduction counter is used for counting R-waves corresponding to depolarizations that in all likelihood have been conducted from the atria. Both of these counters have been previously initialized to a count of 0 upon enabling the pro-arrhythmic monitoring feature (not shown in FIG. 6B).

After increasing either the non-1:1 or the 1:1 conduction counter, method 601 determines if a desired number of measured P-R intervals, Y, have been evaluated at decision step 630. If not, method 601 proceeds to step 435 to continue monitoring P-R intervals during scheduled atrial ATP sequences and for a post-atrial ATP monitoring period. If the desired number of P-R intervals, Y, has been measured and evaluated, method 601 determines if 1:1 or nearly 1:1 conduction is present at decision step 635. In one embodiment, 1:1 conduction or nearly 1:1 conduction is affirmed if a minimum number, X, out of the Y measured P-R intervals represent conduction of atrial activation to the ventricles. The ratio of conducted to non-conducted beats can be determined by comparing the values stored in the 1:1 conduction counter and non-1:1 conduction counter. In one embodiment, if 3 out 4 ventricular depolarizations correspond to atrial activation, then the rhythm is identified as nearly 1:1.

If 1:1 or nearly 1:1 conduction is not detected at decision step 635, then method 601 proceeds to step 435 to continue monitoring for ventricular pro-arrhythmia. If 1:1 conduction is detected at step 635, method 601 determines if this 1:1 conduction is occurring at a ventricular rate greater than some maximum rate limit at decision step 640. The maximum rate limit is the ventricular rate above which 1:1 conduction is considered to be pro-arrhythmic. The maximum rate limit may be a predetermined fixed or programmable value. If the maximum rate limit is not exceeded, the 1:1 counters are reset at step 645 and method 601 returns to step 435. If 1:1 or nearly 1:1 conduction occurs above a maximum ventricular rate limit, the current atrial ATP sequence is immediately aborted at step 447. Method 601 proceeds to step 450 of FIG. 6A to determine if atrial ATP therapies will be temporarily or permanently disabled as described previously in conjunction with FIG. 4A.

It is recognized that while a particular algorithm has been described in conjunction with FIG. 6B for detecting 1:1 or nearly 1:1 conduction during atrial ATP, other methods known in the art for detecting 1:1 or nearly 1:1 conduction patterns may be employed by the present invention.

While the methods described in conjunction with FIGS. 4A through 6B describe algorithms for detecting evidence of proarrhythmia based on ventricular rate acceleration, 1:1 atrial-ventricular conduction, or R-wave morphology changes, it is recognized that other methods for detecting ventricular pro-arrhythmia during or immediately after atrial ATP based on sensing cardiac-related signals may be used in controlling the delivery of atrial ATP therapies. Furthermore, it is contemplated that a combination of criteria relating to ventricular rate, 1:1 conduction patterns, R-wave morphology and/or other ventricular pro-arrhythmia detection criteria may be used in controlling the delivery of atrial ATP therapies.

Figure 7:
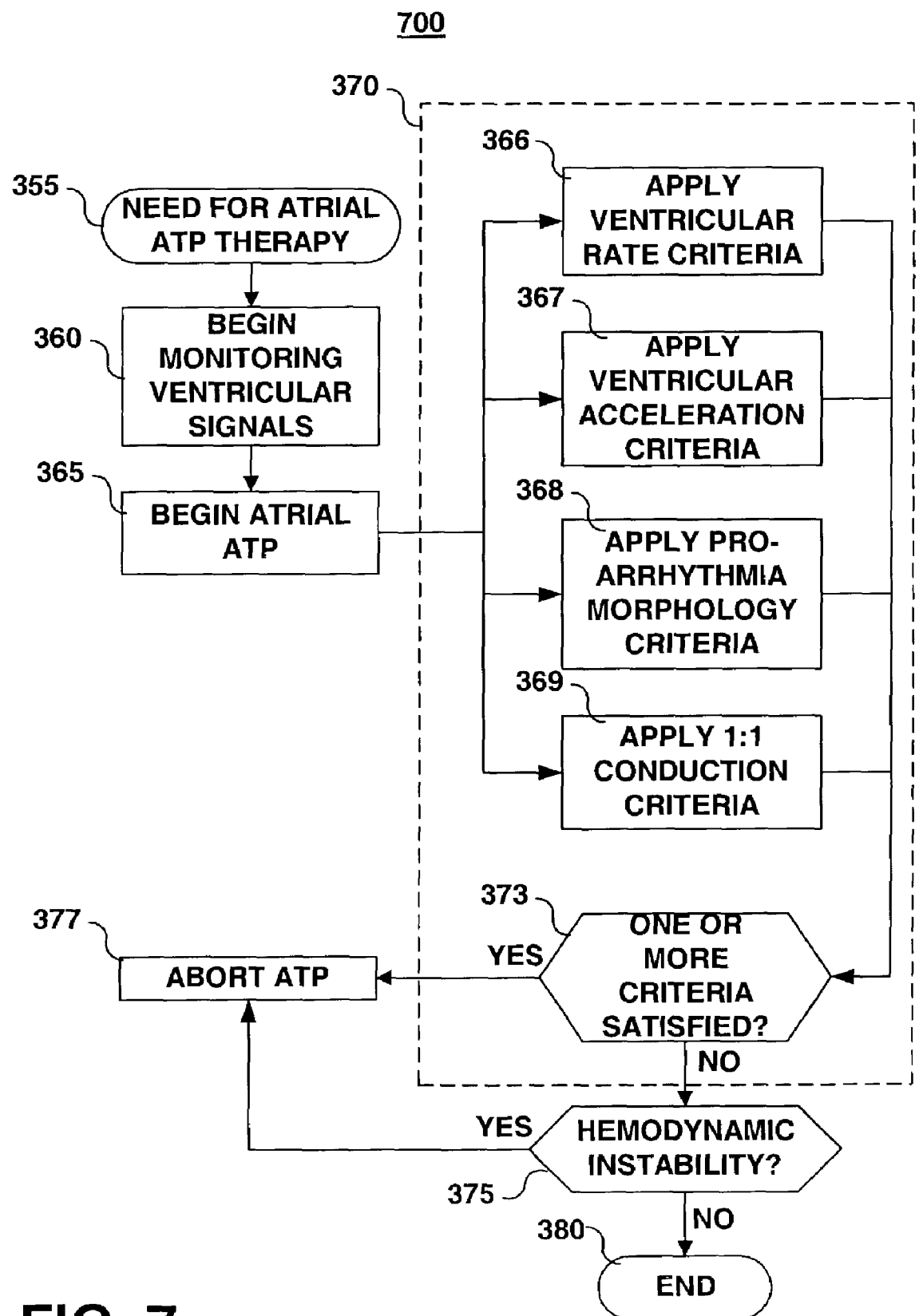
FIG. 7 is a flow chart of a method for controlling atrial ATP therapies based on any of a number of pro-arrhythmia detection criteria.

FIG. 7 is a flow chart providing an overview of a method for controlling atrial ATP therapies based on any of a number of pro-arrhythmia detection criteria. Steps included in method 700 of FIG. 7 correspond to identically labeled steps included in method 350 of FIG. 3. After detecting a need for atrial therapy at step 355, and monitoring ventricular signals for determination of any pre-atrial ATP reference values at step 360, atrial ATP begins at step 365. In method 700, step 370 for detecting ventricular pro-arrhythmic changes includes applying a number of pro-arrhythmia detection criteria upon each sensed R-wave (or measured R-R or P-R interval). Such criteria may include, but are not limited to, fast ventricular rate criteria (step 366), ventricular rate acceleration criteria (step 367), pro-arrhythmia R-wave morphology criteria (step 368) and/or 1:1 conduction criteria (step 369). Each of these criteria may include one or more requirements related to ventricular rate, ventricular rate acceleration, R-wave morphology, or 1:1 conduction, respectively. For example, ventricular rate criteria may require that a running mean or median R-R interval during atrial ATP be less than some minimum interval, indicating a fast ventricular rate. Ventricular rate acceleration criteria may be satisfied according to the algorithms described in conjunction with methods 400 or 401 of FIGS. 4A and 4B, respectively. R-wave morphology criteria may be satisfied according to the algorithms described in conjunction with method 500 of FIG. 5, and 1:1 conduction criteria may be satisfied according to the algorithms described in conjunction with method 600 or 601 of FIGS. 6A and 6B, respectively.

It is further contemplated that pro-arrhythmia detection criteria may be defined according to statistical evaluations of sensed cardiac activity rather than using specified thresholds or ranges for delineating pro-arrhythmic activity from normal activity. For example, rather than using a specified increase in ventricular rate, a change in the statistical distribution of ventricular intervals before atrial ATP could be compared with that during and after atrial ATP, using a statistical approach, rather than one based on a simple rate change.

Monitoring of ventricular signals during atrial ATP therapies may be performed for detecting evidence of ventricular pro-arrhythmia according to any of the prescribed criteria in a simultaneous or approximately simultaneous manner. If any one or more criteria are satisfied at decision step 373, the current atrial ATP sequence is aborted at step 377. In the embodiment shown in FIG. 7, an optional step 375 for detecting hemodynamic instability simultaneous with or immediately after ATP delivery is included. If hemodynamic instability is detected based on a cardiac-related signal, such as a drop in blood pressure or a reduction in ventricular wall motion, during ATP delivery or a post-atrial ATP monitoring period, atrial ATP therapy is aborted at step 375. If none of the ventricular pro-arrhythmia criteria are satisfied during atrial ATP or during a post-atrial ATP monitoring period, and hemodynamic instability is not detected at step 375, method 700 is terminated at step 380.

It is further contemplated that criteria for detecting evidence of ventricular pro-arrhythmia may be prioritized such that if a high priority criteria is satisfied, ATP therapy is immediately aborted, whereas satisfaction of a relatively low priority criteria may require satisfaction of additional criteria before aborting the atrial ATP therapy.

While the present invention has been described with regard to monitoring the ventricular response to atrial ATP, it is further contemplated that aspects of the present invention could be adapted for use in controlling the delivery of multi-site or multi-chamber therapies wherein a therapy is delivered at one or more sites or in one or more chambers and cardiac signals are monitored at one or more different sites in the same or different heart chambers for detecting a pro-arrhythmic response.

Some of the techniques described above may be embodied as a computer-readable medium comprising instructions for a programmable processor such as microprocessor 224 or pacer timing/control circuitry 212 shown in FIG. 2. The programmable processor may include one or more individual processors, which may act independently or in concert. A "computer-readable medium" includes but is not limited to read-only memory, Flash memory and a magnetic or optical storage medium. The medium includes instructions for causing a processor to perform the method for disabling or aborting the delivery of atrial anti-tachycardia pacing therapies upon detecting evidence of ventricular pro-arrhythmia, described above.

Thus, an implantable cardioverter defibrillator system and method have been described for controlling atrial ATP delivery based on monitoring for ventricular pro-arrhythmia associated with atrial ATP therapies. While the present invention has been described according to specific embodiments presented herein, these embodiments are intended to be exemplary, not limiting, with regard to the following claims.

The invention claimed is:

1. An implantable medical device, comprising:
a therapy delivery circuit to generate a therapy;
a sensing circuit to receive cardiac signals;
a plurality of electrodes coupled to the sensing circuit and the therapy delivery circuit sensing cardiac signals and delivering the therapy; and
control circuitry coupled to the therapy delivery circuit and the sensing circuit, the control circuitry configured to receive cardiac signals from the sensing circuit, determine a need for delivering the therapy, initiate the therapy within a first chamber of a heart in response to the determined need, detect pro-arrhythmia in a second chamber of the heart different from the first chamber in response to the cardiac signals, the detected pro-arrhythmia occurring in the second chamber in response to the delivered therapy in the first chamber, and to control the therapy delivery in the first chamber in response to the pro-arrhythmia being detected in the second chamber, wherein the therapy corresponds to atrial pacing and the control circuitry detects ventricular pro-arrhythmia and terminates the therapy delivery in response to the ventricular pro-arrhythmia being detected, and wherein the control circuitry is further configured to detect an approximately 1:1 conduction pattern between the atrium and ventricles of the heart in response to the sensed cardiac signals, wherein the ventricular pro-arrhythmia is detected in response to detecting the approximately 1:1 conduction pattern.

2. The device of claim 1, further comprising a telemetry circuit to receive an external input, wherein the control circuitry determines the need for delivering the therapy and initiates the therapy in response to receipt of the external input.

3. The device of claim 1, wherein the control circuitry is further configured to determine one of a ventricular rate, an R-wave morphology, and an atrial-ventricular conduction pattern in response to the cardiac signals and wherein the ventricular pro-arrhythmia is detected in response to changes in one of the ventricular rate, R-wave morphology, and atrial-ventricular conduction patterns.

4. The device of claim 1, wherein the sensed cardiac signals comprise signals sensed subsequent to the therapy delivery and the control circuitry detects the pro-arrhythmia in response to the sensed cardiac signals sensed subsequent to the therapy delivery.

5. The device of claim 1, wherein the plurality of electrodes include leadless electrodes.

6. The device of claim 1, further comprising a storage device storing ventricular pro-arrhythmia detections associated with the delivered therapy.

7. The device of claim 1, wherein the control circuitry determines when the ventricular pro-arrhythmia is no longer detected and re-initiates the therapy in response to ventricular pro-arrhythmia no longer being detected.

8. An implantable medical device, comprising:
a therapy delivery circuit to generate a therapy;
a sensing circuit to receive cardiac signals;
a plurality of electrodes coupled to the sensing circuit and the therapy delivery circuit sensing cardiac signals and delivering the therapy; and
control circuitry coupled to the therapy delivery circuit and the sensing circuit, the control circuitry configured to receive cardiac signals from the sensing circuit, determine a need for delivering the therapy, initiate the therapy within a first chamber of a heart in response to the determined need, detect pro-arrhythmia in a second chamber of the heart different from the first chamber in response to the cardiac signals, the detected pro-arrhythmia occurring in the second chamber in response to the delivered therapy in the first chamber, and to control the therapy delivery in the first chamber in response to the pro-arrhythmia being detected in the second chamber, wherein the sensed cardiac signals comprise signals sensed before initiating therapy delivery and subsequent to initiating therapy delivery,
wherein the control circuitry determines a reference metric associated with the sensed cardiac signals sensed before initiating therapy delivery, determines a metric associated with the sensed cardiac signals sensed subsequent to initiating therapy delivery, wherein the pro-arrhythmia is detected in response to the metric associated with sensed cardiac signals sensed subsequent to initiating therapy delivery being substantially different than the reference metric.

9. An implantable medical device, comprising:
a therapy delivery circuit to generate a therapy;
a sensing circuit to receive cardiac signals;
a plurality of electrodes coupled to the sensing circuit and the therapy delivery circuit sensing cardiac signals and delivering the therapy;
control circuitry coupled to the therapy delivery circuit and the sensing circuit, the control circuitry configured to receive cardiac signals from the sensing circuit, determine a need for delivering the therapy, initiate the therapy within a first chamber of a heart in response to the determined need, detect pro-arrhythmia in a second chamber of the heart different from the first chamber in response to the cardiac signals, the detected pro-arrhythmia occurring in the second chamber in response to the delivered therapy in the first chamber, and to control the therapy delivery in the first chamber in response to the pro-arrhythmia being detected in the second chamber; and
a storage device storing ventricular pro-arrhythmia detections associated with the delivered therapy, wherein the therapy is an anti-tachycardia pacing therapy and corresponds to atrial pacing, and the control circuitry detects ventricular pro-arrhythmia and terminates the therapy delivery in response to the ventricular pro-arrhythmia being detected, and further comprising a counter to count a number of times the therapy is terminated, wherein the control circuitry is further configured for permanently disabling the therapy when the counter reaches a permanent disable value.

* * * * *